United States Patent [19]

Robison et al.

[11] Patent Number: 4,981,794

[45] Date of Patent: Jan. 1, 1991

[54] METHOD OF PREPARING D(−)-β-HYDROXYISOBUTYRIC ACID BY FERMENTATION

[75] Inventors: Robert S. Robison, North Brunswick; Laszlo J. Szarka, East Brunswick, both of N.J.

[73] Assignee: E. R. Squibb & Sons, Inc., Princeton, N.J.

[21] Appl. No.: 110,166

[22] Filed: Oct. 19, 1987

Related U.S. Application Data

[63] Continuation-in-part of Ser. No. 689,111, Jan. 7, 1985, abandoned, which is a continuation-in-part of Ser. No. 574,507, Jan. 27, 1984, abandoned.

[51] Int. Cl.$^5$ .............................................. C12P 7/42
[52] U.S. Cl. ................................. 435/146; 435/911; 435/922
[58] Field of Search ........................ 435/146, 911, 922

[56] References Cited

U.S. PATENT DOCUMENTS

| | | | |
|---|---|---|---|
| 4,211,846 | 7/1980 | Lafferty | 435/146 |
| 4,310,635 | 1/1982 | Hasegawa et al. | 435/146 |
| 4,433,053 | 2/1984 | Hughes et al. | 435/146 |
| 4,618,583 | 10/1986 | Robison et al. | 435/146 |

FOREIGN PATENT DOCUMENTS

| | | | |
|---|---|---|---|
| 178726 | 6/1981 | Japan | 435/146 |
| 0158188 | 9/1983 | Japan | 435/146 |

OTHER PUBLICATIONS

Chemical Abstracts, vol. 101, 1984, p. 421, Abstract No. 226524q.

*Primary Examiner*—Jacqueline Stone
*Assistant Examiner*—Marian C. Knode
*Attorney, Agent, or Firm*—Burton Rodney

[57] ABSTRACT

A method is provided for preparing D(−)-β-hydroxyisobutyric acid by fermentation employing the methyl and/or ethyl esters of isobutyric acid, the methyl and/or ethyl esters of methacrylic acid, isobutyl isobutyrate and/or isobutyl methacrylate as the substrate and a microorganism of the genus Candida and other fungi. In an alternative method, the isolated cells of the various microorganisms are employed with one or mixtures of the above substrates.

21 Claims, No Drawings

METHOD OF PREPARING D(—)-β-HYDROXYISOBUTYRIC ACID BY FERMENTATION

REFERENCE TO OTHER APPLICATIONS

This application is a continuation-in-part of application Ser. No. 689,111, filed Jan. 7, 1985 now abandoned, which is a continuation-in-part of application Ser. No. 574,507, filed Jan. 27, 1984, now abandoned.

FIELD OF THE INVENTION

The present invention relates to a method for preparing D(—)-β-hydroxyisobutyric acid using as the substrate esters of isobutyric acid or methacrylic acid.

BACKGROUND OF THE INVENTION

D(—)-β-hydroxyisobutyric acid is used in the preparation of captopril, an angiotensin-converting enzyme inhibitor useful in the treatment of hypertension.

Until now, the preparation of D(—)-β-hydroxyisobutyric acid has been accomplished by chemical synthesis and through the use of fermentation techniques.

With respect to chemical synthesis, β-hydroxyisobutyric acid has been prepared from formaldehyde and ethyl [-bromopropionate by the Reformatsky reaction (E. E. Blaise et al., *Ann. Chim. et Phys.* 17,371, 1969) whereby the optically inactive DL(±) form is obtained. Chemical resolution is employed to obtain the optically active D-(—) form (J. Retey et al., *Biochemische Zeitschrift*, 342, 256–271, 1965. In *Journal of Biological Chemistry*, 241, 868, 1966, M. Specter et al. disclose a method for obtaining the optically active D(—) form directly without need for optical resolution employing threo-3-methyl-L-aspartic acid as the starting material. Unfortunately, however, the procedure is complicated and expensive to carry out.

U.S. Pat. No., 4,310,635 to Hasegawa et al. discloses a fermentation method wherein isobutyric acid or methacrylic acid is converted into D(—)-β-hydroxyisobutyric acid employing microorganisms, including those of the Candida genus such as *Candida rugosa* IFO 0750 and *Candida rugosa* IFO 0591, and appropriate culture broths. The product is isolated from the culture broth by solvent extraction and ion exchange, wherein the culture broth or reaction medium is acidified with a mineral acid such as sulfuric acid or hydrochloric acid, an inorganic salt is added, if necessary, to increase the ionic strength of the broth or mixture and a water-immiscible solvent such as butanol, methyl-isobutyl ketone or ethyl acetate is used to extract the product.

Japanese patent No. 178726 dated June 11, 1981 and assigned to Kanegafuchi Chem KK discloses a method for preparing D(—)-β-hydroxyisobutyric acid by reacting isobutyl aldehyde, isobutylamine, or isobutyl alcohol with Candida, (such as *Candida rugosa*), Pichia, Torulopsis, Aspergillus, Choanephora, Wingea or Zygorhynchus. The patentee indicates good yield is obtained at a lower cost than obtained through optical resolution of DL(±)-β-hydroxy- isobutyric acid or asymmetrical oxidation of 2-methyl-1,3-propanediol or the fermentation process using isobutyric acid or methacrylic acid.

BRIEF DESCRIPTION OF THE INVENTION

In accordance with the present invention, there is provided a fermentation method for preparing the optically active D(—)-β-hydroxyisobutyric acid, which method includes the steps of subjecting a substrate which has poor water solubility, namely, the methyl and/or ethyl esters of isobutyric acid, the methyl and/or ethyl esters of methacrylic acid, isobutyl-isobutyrate and/or isobutyl methacrylate to the action of a microorganism capable of converting one or more of the above substrates into D(—)-β-hydroxyisobutyric acid. The above reaction may be carried out in several different ways. In a preferred embodiment, the microorganism is cultivated aerobically in an aqueous nutrient medium containing all or a portion of the substrate so that cultivation of the microorganism and subjection of such portion of the substrate (present in the medium) to the action of the microorganism are carried out simultaneously. After a predetermined period and/or predetermined concentration of product is obtained, the remainder of the substrate, if any, is added, and the fermentation is continued until a desired concentration of product is obtained.

In alternative embodiments, the microorganism is first cultivated in an aqueous nutrient medium, then the substrate is added to the resulting culture broth or to a suspension of cells obtained through the initial cultivation, and the mixture is then incubated aerobically.

As indicated, the method of the invention employs a substrate which has poor water solubility, namely, methyl and/or ethyl esters of isobutyric acid, methyl and/or ethyl esters of methacrylic acid, isobutyl-isobutyrate and/or isobutyl methacrylate. Accordingly, it would appear that higher substrate concentrations may be used than in prior art fermentation techniques such as disclosed in U.S. Pat. No. 4,310,635, so that higher product concentrations may be obtainable in the method of the invention over prior art processes.

It is also possible to use significantly higher (poorly water-soluble) substrate concentrations than with the water-soluble substrates of U.S. Pat. No. 4,310,635 since the microbial toxicity of the poorly water-soluble substrates as used in the present invention is substantially less than that of the water-soluble substrates.

In addition, in the method of the invention, each mole of poorly water-soluble ester substrate (such as isobutyl-isobutyrate or isobutyl methacrylate) yields 2 moles of D(—)-β-hydroxyisobutyric acid while only 1 mole of D(—)-β-hydroxyisobutyric acid can be generated per mole of water-soluble isobutyric acid or methacrylic acid as disclosed in U.S. Pat. No. 4,310,635.

Furthermore, for product recovery, a solvent extraction technique can be used that will result in the efficient separation of unutilized poorly water soluble substrates from D(—)-β-hydroxy isobutyric acid without the need for fractionation either by vacuum distillation or column chromatography (the latter being required when water-soluble substrates are used). The unutilized ester substrate can then be recycled for further product formation.

DETAILED DESCRIPTION OF THE INVENTION

The microorganism preferably employed in carrying out the method of the present invention will be of the genus Candida, and preferably of the strain *Candida rugosa*, for example, ATCC #20116. However, other microorganisms may be employed which may be selected by the screening procedure as disclosed in U.S. Pat. No. 4,310,635 using methyl and/or ethyl esters of isobutyric acid and/or methyl and/or ethyl esters of methacrylic acid and/or isobutyl-isobutyrate and/or isobutyl-methacrylate in place of isobutyric acid or methacrylic acid.

Examples of other microorganisms which may be employed herein belong to the genera Torulopsis, Trygonopsis, Saccharomyces, Pichia, Debaryomyces, Wingea, Rhodosporidium, Aspergillus, Choanephora, and Zygorhynchus. Among microorganisms belonging to the genera illustrated above, the following strains, for example, may be employed in the present invention: *Candida parapsilosis, Candida utilis, Torulopsis candida, Trygonopsis variabilis, Saccharomyces cerevisiae, Saccharomyces rouxii, Pichia membranaefaciens, Debaryomyces hansenii, Wingea robertsii, Rhodosporidium toruloides, Aspergillus niger, Choanephora circinanus* and *Zygorhynchus moelleri.*

As indicated, for subjecting the substrate to the action of the microorganism, essentially two techniques are available. In a first technique, the microorganism is cultivated aerobically in an aqueous medium containing all or a portion of the substrate from the beginning of the cultivation, thereby accumulating D(−)-β-hydroxyisobutyric acid in the medium simultaneously with propagation of the microorganism. In the other technique, the process consists of two steps, that is, cultivation of the microorganism and subjection of the substrate to the action of the microorganism.

The first step of the two-step process can be carried out by cultivating the microorganism in an aqueous nutrient medium and recovering the cells. The second step of the two-step process can be carried out by adding the substrate to a suspension of the recovered cells or to immobilized cells in suitable aqueous buffer or medium followed by incubating the resulting mixture aerobically for all or part of the reaction time at a pH from about 6.0 to about 9.5 and at a temperature of from about 20° to about 40° C.

Since enzymes of microorganisms are involved in the reaction of the process of the present invention, the separated cells can also be subjected to various treatments, such as drying and homogenization, etc., before suspension in an appropriate aqueous medium in order to promote the enzyme reaction. Therefore, use of cells treated in various ways should be construed as being covered by the scope of the present invention.

In carrying out the method wherein the microorganism is cultivated aerobically in an aqueous medium containing all or part of the substrate, reaction may be carried out by adding all or a portion of the substrate prior to growing the culture. The portion of substrate added to the culture prior to fermentation comprises from about 0.05 to about 0.2% and preferably from about 0.1 to about 0.15% by weight of the volume of aqueous medium to be used. The pH of the medium is adjusted, if necessary, to within the range of from about 4 to about 9.5, and preferably from about 6 to about 9, by adding as needed either strong inorganic base such as NaOH or KOH or strong inorganic acid such as HCl or $H_2SO_4$, while the reaction mixture is maintained at a temperature of from about 20° to about 40° C. The microorganism is cultivated aerobically and after a predetermined period of from about 12 to about 30 hours, and preferably from about 20 to about 25 hours, the remainder of the substrate is added. After addition of substrate is completed, the pH of the broth is adjusted within the range of from about 6 to about 9.5 and preferably from about 7 to about 8.5 by adding strong bases as described above. The fermentation is allowed to proceed for a total period of from about 40 to about 120 hours and preferably from about 48 to about 72 hours, until a concentration of product of from about 0.2 to about 1.5%, and preferably from about 0.5 to about 1.5% by volume of the broth is achieved.

Another embodiment of the method of the invention includes the steps of adding all of the substrate material after the microorganism is cultured in the culture medium to provide an initial broth concentration of substrate of within the range of from about 1 to about 4% by weight and preferably from about 2 to about 3% by weight based on the total volume of the culture medium or broth, maintaining the pH of the broth between from about 6 to about 9.5 and preferably from about 7 to about 8.5 by adding strong base such as KOH or NaOH, while maintaining the broth at a temperature of from about 20° to about 40° C., and allowing fermentation to continue for a period within the range of from about 40 to about 120 hours and preferably from about 48 to about 72 hours until a peak concentration of product of from about 0.2 to about 1.5% and preferably from about 0.5 to about 1.5% by volume of the broth is achieved.

The fermentation media employed in the method of the invention includes a nitrogen source, a carbon/energy source, and optionally one or more inorganic salts for process control.

The nitrogen source will be present in an amount within the range of from about 0.1 to about 3%, and preferably from about 1 to about 2% by weight of the media. Examples of suitable nitrogen sources include casein hydrolysate, cottonseed or its derivatives, corn steep liquor, soybean meal, organic and inorganic compounds, such as $NH_4Cl$, $(NH_4)_2SO_4$, ammonia water, urea, amino acids, meat peptone and hydrolysates of soy bean meal or any other comparable organic or inorganic N sources or their soluble derivatives.

The carbohydrate source will be present in the fermentation media in an amount within the range of from about 0.5 to about 5% and preferably from about 1 to about 3% by weight. Examples of suitable carbohydrate sources include starch, dextrin, maltose, lactose, glucose, glycerol, molasses, and the like, organic acids, such as acetic acid, fumaric acid and lactic acid, alcohols such as methanol, ethanol and propanol, liquid hydrocarbons, such as n-paraffins and olefins, oils and fats and the like.

The fermentation media employed in the method of the invention may optionally include other conventional fermentation medium components such as one or more inorganic salts which aid in process control. Examples of such inorganic salts include, but are not limited to, $CaCO_3$, $CuSO_4$, NaCl, $(NH_4)_2HPO_4$, $ZnSO_4$, $FeSO_4$, $MgSO_4$, $MnSO4$ or $Na_2HPO_4$ including hydrates thereof. The fermentation media may also contain one or more antifoam agents such as silicone antifoam.

A preferred fermentation medium formulation includes from about 1 to about 2% by weight of a nitrogen source, preferably a mixture of an organic and inorganic nitrogen, such as yeast extract and ammonium nitrate or ammonium sulfate, from about 1 to about 3% by weight of glucose as the carbohydrate source, optionally from about 0.01% to about 1% by weight of one or more inorganic salts, such as potassium dihydrogen phosphate and magnesium sulfate, and optionally from about 0.01 to 0.2% by weight of a silicone antifoam.

The D(−)-β-hydroxyisobutyric acid product may be isolated from the culture broth or reaction mixture by subjecting the reaction mixture to filtration or centrifugation and then solvent extraction techniques. Two methods of extraction may be used. In the first extraction method, the clarified culture broth or reaction mixture is acidified with a mineral acid, such as $H_2SO_4$ or HCl, to adjust pH to within the range of from about 1 to about 4 and preferably from about 2 to about 3. Inorganic salt such as $(NH_4)_2SO_4$, $Na_2SO_4$, NaCl or $MgSO_4$ is added to increase ionic strength of the broth or mixture, and the mix is extracted with a water-immiscible solvent such as ethyl acetate, butanol or methyl isobutyl ketone. The desired product is obtained by distilling off the solvent and subjecting the residue to fractionation by, for example, vacuum distillation at a temperature in the range of 100°–110° C., or by column chromatography.

In the alternative method, the pH of the clarified culture broth or aqueous reaction mixture is adjusted to within the range of from about 8 to about 10 with either NaOH or KOH. The unutilized ester substrate is then extracted from the aqueous reaction mixture with a water-immiscible solvent such as ethyl acetate or methyl isobutyl ketone and recovered by evaporating the solvent. The pH of the aqueous phase is then adjusted with either $H_2SO_4$ or HCl, to within the range of from about 1 to about 4 and preferably from about pH 2 to about 3. Inorganic salts such as $(NH_4)_2SO_4$, $Na_2SO_4$, $MgSO_4$ or NaCl are then added to increase the ionic strength of the solution and the D(−)-β-hydroxyisobutyric acid is extracted with a water immiscible solvent such as ethyl acetate or methyl isobutyl ketone. The desired product in high purity is obtained by distilling off the solvent.

The following Examples represent preferred embodiments of the present invention. All temperatures are expressed in degrees Centigrade.

EXAMPLE 1

Preparation of D(−)-β-Hydroxyisobutyric Acid Using Ethyl Methacrylate Substrate

10 Liters of the following medium were sterilized in a 14-liter glass fermentor after adjusting the pH of the medium to 7.5.

| Ingredient | Ingredient |
| --- | --- |
| Cerelose - 3.3% | $ZnSO_4.7H_2O$ - 0.006% |
| Yeast Extract - 0.3% | $FeSO_4.7H_2O$ - 0.009% |
| $(NH_4)_2HPO_4$ - 1.3% | $CuSO_4.5H_2O$ - 0.0005% |
| $KH_2PO_4$ - 0.7% | $MnSO_4.4H_2O$ - 0.001% |
| $MgSO_4.7H_2O$ - 0.08% | NaCl - 0.01% |
| Ucon Lubricant - 0.05% (silicone-type defoamer) | |

The glass fermentor was equipped with an agitator and sparger. The fermentor was operated at 30° C., and sterile air was supplied at 1 vol/vol medium/minute. The agitator speed was 500 rpm during the first 14 hours, and then 300 rpm until harvest. After the medium had been sterilized and cooled to 30° C., the pH was adjusted to 7.3 with sodium hydroxide. 500 cc of a 24-hour broth culture of *Candida rugosa* ATCC #20116 was then used to inoculate the fermentor. After 23 hours, 200 ml of ethyl methacrylate was added to provide an initial broth concentration of ethyl methacrylate of 2%, and the pH was adjusted to 8 to 8.5 with sodium hydroxide. At log 39, additional sodium hydroxide was added to adjust the pH to 8.5.

The synthesis of hydroxyisobutyric acid was followed by HPLC on clarified supernatants of the broth. After 49 hours of fermentation, the broth was found to contain 0.49% of hydroxyisobutyric acid. The hydroxyisobutyric acid was extracted with ethyl acetate after the clarified broth had been adjusted to a pH of 2.5 and saturated with ammonium sulfate. The ethyl acetate was removed by distillation. The oil residue was further purified by high vacuum distillation (0.2 mm) at 106°–108° C. The optical rotation of the distillate fraction recovered after high vacuum distillation was found to be $[\alpha]_D^{23°}$ −14.6. This established that the hydroxyisobutyric acid had the desired D(−)-rotation while mass spectrometry indicated that the major component of this residue has a molecular weight of 104.

EXAMPLES 2 TO 6

Preparation of D(−)-β-Hydroxyisobutyric Acid Using Methyl Isobutyrate, Ethyl Isobutyrate, Methyl Methacrylate, Isobutyl Isobutyrate or IsobutylMethacrylate as the Substrate Following the procedure of Example 1 except substituting methyl isobutyrate (Example 2), ethyl isobutyrate (Example 3), methyl methacrylate (Example 4), isobutyl-isobutyrate (Example 5) or isobutyl-methacrylate (Example 6) for ethyl methacrylate, D(−)-β-hydroxyisobutyric acid is obtained.

EXAMPLE 7

Preparation of D(−)-β-Hydroxyisobutyric Acid Wherein Methyl Isobutyrate is Added to a Cell Suspension Obtained from a Fermentation Broth

*Candida rugosa* ATCC #20116 was inoculated into 20 L of a medium containing 2.0% glucose, 0.5% yeast extract, 0.3% peptone, 0.3% meat extract, 0.1% isobutyric acid and 0.05% Ucon Lubricant as a defoamer. The fermentation was conducted in a 38 L fermentor at 30° C., at a pH 6.0 and with 20 SLPM of air and agitation at 250 RPM. After 24 hours, the resulting cells, 5 g/liter of medium, were recovered by centrifugation, washed twice with 0.1% saline solution and suspended in 1/15 M pH 8.5 phosphate buffer.

To 100 ml of this cell suspension was added 3 g of methyl isobutyrate. The resulting mixture was incubated at 30° C. and the synthesis of hydroxyisobutyric acid was followed by HPLC. After 40 hours of incubation, 0.4% of hydroxyisobutyric acid was synthesized.

EXAMPLES 8 To 12

Preparation of D(−)-β-Hydroxyisobutyric Acid Using Ethyl Isobutyrate, Methyl Methacrylate, Ethyl Methacrylate, Isobutyl Isobutyrate or Isobutyl Methacrylate as Substrates with Washed Cell Suspensions of *Candida rugosa*

Following the procedure of Example 7 except substituting ethyl isobutyrate (Example 8), methyl methacrylate (Example 9), ethyl methacrylate (Example 10), isobutyl-isobutyrate (Example 11) or isobutyl methacrylate (Example 12) for methyl isobutyrate, D(−)-β-hydroxyisobutyric acid is obtained.

EXAMPLE 13

Preparation of D(−)-β-Hydroxyisobutyric Acid Using Isobutyl-Isobutyrate

175 Liters of the following medium were sterilized in a 250 liter stainless steel fermentor equipped with an agitator and sparger after adjusting the pH of the medium to 8.5.

| Ingredient* | Ingredient |
|---|---|
| Cerelose - 4.4% | $ZnSO_4.7H_2O$ - 0.006% |
| Yeast Extract - 0.3% | $FeSO_4.7H_2O$ - 0.009% |
| $(NH_4)_2HPO_4$ - 1.3% | $CuSO_4.5H_2O$ - 0.0005% |
| $KH_2PO_4$ - 0.7% | $MnSO_4.4H_2O$ - 0.001% |
| $MgSO_4.7H_2O$ - 0.08% | NaCl - 0.01% |
| Sag Defoamer - 0.15% | |

*Weight by volume

The medium after sterilization was cooled to 30° C. Agitation was adjusted to 250 rpm while air was introduced through the sparger at a rate of 1.0 volume of air per volume of medium per minute. The fermentor was then inoculated with 7.0 liters of *Candida rugosa* ATCC20116 inoculum grown in the same medium in a germinator tank for 15 hours.

After 11 hours, the pH of the growing culture was adjusted to 8.0 and the broth was aerated only by air flowing over the surface of the agitated broth. Immediately thereafter 30 cc of isobutylisobutyrate was fed into the broth every 5 minutes. The feed of isobutyl-isobutyrate continued for 15 hours during which time the pH of the broth was adjusted to 8.0 at periodic intervals. When a total of 3.0% v/v of isobutyl-isobutyrate had been added, the fermentation was continued for an additional 9 hours with the air overlay. The pH was then adjusted to 7.5 and the broth was aerated only from the sparger. At periodic intervals, thereafter, samples were withdrawn from the fermentor for analysis.

The synthesis of hydroxyisobutyric acid from isobutyl-isobutyrate was followed by HPLC analysis of ethyl acetate extracts of the broth. After 154 hours of fermentation, the broth was found to contain 0.7% hydroxyisobutyric acid. The hydroxyisobutyric acid was isolated by the steps comprising centrifugation, saturation of the cell free broth with ammonium sulfate, adjusting the pH to 2.0 with sulfuric acid followed by extraction with ethyl acetate. The ethyl acetate was removed by vacuum distillation at 40° C. leaving an oily residue. The oily residue was dissolved in a 9:1 solution of toluene in acetone. The hydroxyisobutyric acid was isolated from this solution by column chromatography on activated silica gel. Fractions containing hydroxyisobutyric acid, based on HPLC analysis, were pooled and the toluene acetone was removed by distillation. The optical rotation of a 2% w/v methanolic solution of the residue was found to be $[\alpha]_D^{23}$ −18.6.

This established that the hydroxyisobutyric acid synthesized from isobutyl-isobutyrate had the desired D(−) optical configuration. Mass spectrometry indicated that the molecular weight of the major component (104) was that of hydroxyisobutyric acid.

EXAMPLE 14

Isobutyric acid (adjusted to pH 7) and isobutyl-isobutyrate were tested for their comparative minimal inhibitory concentrations (MICs) versus the fungi *Aspergillus niger*, *Canadida rugosa* and *Saccharomyces cerevisiae*. Both test compounds are added to the media which may be used for the synthesis.

The results of the MIC determinations, carried out using a Beckman Biomek robot, are presented herein.

Materials

A. Media
1. K57 with 0.125% agar

| Ingredient | ml or g/L |
|---|---|
| Cerelose | 33 g |
| Yeast extract | 3 g |
| Mineral salts solution* | 100 ml |
| Agar | 1.25 g |
| Tap water | 900 ml |
| pH | 7.8 |

| Ingredient | g/L |
|---|---|
| $(NH_4)_2HPO_4$ | 130 |
| $KH_2PO_4$ | 70 |
| $MgSO_4.7H_2O$ | 8 |
| $ZnSO_4.7H_2O$ | 0.6 |
| $FeSO_4.7H_2O$ | 0.9 |
| $CuSO_4.5H_2O$ | 0.05 |
| $MnSO_4.4H_2O$ | 0.1 |
| NaCl | 1.0 |

2. BA-76 with 0.2% agar

| Ingredient | g/L |
|---|---|
| Peptone, BBL | 9.4 |
| Yeast extract | 4.7 |
| Beef extract | 2.4 |
| NaCl | 10 |
| Glucose | 10 |
| Agar | 2 |
| pH | 6.1 |

B. Buffer
1. BA-40 pH 6.0 Buffer

| Ingredient | g/L |
|---|---|
| $K_2HPO_4$ | 22.48 g |
| $KH_2PO_4$ | 8.528 g |

C. Fungi
1. *Aspergillus niger* ATCC 16404
2. *Candida rugosa* SC6792-V2A
3. *Saccharomyces cerevisiae* ATCC 2601

*Composition of mineral salts solution

Method

1. The Beckman robot performed:
(1) Serial two-fold dilutions of the two compounds in quadruplicate using 25 μl of each compounds and 25 μl of the diluent BA-40, mixing at each dilution step. The dilutions were carried out in Falcon microtiter plates.
(2) Addition and mixing of 200 μl of inoculated medium per well.
Note:
Fifty ml of medium tempered to 50° C. were inoculated with 100 μl of an overnight broth culture of *C. rugosa*, *S. cerevisiae* or a saline-wash of an *A. niger* slant.
These cultures had at least $10^8$ CFU/ml.
2. The plates were covered, chilled at 2° to 5° C. for 15 minutes, and incubated in a 30° C. waterbath for about 20 hours.
3. Absorbance of each well was recorded at 600 nm by the robot as an indication of turbidity.
4. The end point was determined as the last dilution that resulted in "clear" wells.

Results and Conclusions

The results, summarized in Table 1, show that the ester isobutyl-isobutyrate is substantially less inhibitory than the acid isobutyric acid, towards the growth of the strains of A. niger, C. rugosa and S. cerevisiae tested in this experiment.

TABLE 1

Dilution end points of isobutyl-isobutyrate and isobutyric acid in two media versus three fungal species.

| Compound | Medium | Dilution end point versus | | |
|---|---|---|---|---|
| | | A. niger | C. rugosa | S. cervisiae |
| Isobutyl-isobutyrate | BA-76 | — | 4 | 4 |
| | K57 | No inhibition | No inhibition | No growth in positive controls |
| Isobutyric acid | BA-76 | — | 8 | 16 |
| | K57 | 8 | 8 | No growth in positive controls |

With regard to C. rugosa, it is seen that isobutyl-isobutyrate is 2 times (using BA-76) or at least 8 or more times (using K57) less inhibitory than the isobutyric acid, towards the growth of such organism.

With regard to A. niger, using K-57, it is seen that isobutyl-isobutyrate is at least 8 times less inhibitory than the isobutyric acid, towards the growth of such organism.

With regard to S. cerevisiae, using BA-76, it is seen that isobutyl-isobutyrate is 4 times less inhibitory than the isobutyric acid, towards the growth of such organism.

What is claimed is:

1. A method for producing D(−)-β-hydroxyisobutyric acid, which comprises subjecting a waterinsoluble substrate which is isobutylisobutyrate to the action of a microorganism having the ability to convert the substrate into D(−)-β-hydroxyisobutyric acid in an aqueous medium and recovering D(−)-β-hydroxyisobutyric acid from the medium, wherein the microorganism belongs to the genus selected from the group consisting of the genus Candida, Saccharomyces, and Aspergillus.

2. The method according to claim 1 wherein said microorganism belongs to the species Candida rugosa, Saccharomyces cerevisiae, or Aspergillus niger.

3. The method according to claim 1 wherein said microorganism belongs to the species Candida rugosa.

4. The method according to claim 1 wherein the microorganism is cultivated aerobically in an aqueous medium containing the substrate.

5. The method according to claim 4 wherein the cultivation is carried out at a pH of from about 4 to about 9.5 at a temperature of from about 20° C. to about 40° C.

6. The method according to claim 1 wherein the substrate is added to a culture broth obtained by cultivating the microorganism in an aqueous medium and then the resulting mixture is incubated aerobically.

7. The method according to claim 6 wherein a small amount of said substrate is added in the aqueous medium when the microorganism is cultivated to induce the formation of enzymes by the microorganism.

8. The method according to claim 4 wherein the microorganism is cultivated at a pH of from about 4.0 to about 9.5 and a temperature of from about 20° C. to about 40° C. and the reaction mixture is incubated at a pH of from about 6.0 to about 9.5 and a temperature of from about 20° C. to about 40° C.

9. The method according to claim 1 wherein the substrate is added to a cell suspension prepared by separating cells from a culture broth obtained by cultivating the microorganism in an aqueous medium followed by suspending the cells in an aqueous medium and then the resulting mixture is incubated aerobically for all or a part of the reaction time.

10. The method according to claim 9 wherein the separated cells are immobilized on a suitable carrier before contact with the substrate.

11. The method according to claim 9 wherein a small amount of said substrate is added in the aqueous medium when the microorganism is cultivated to induce the formation of the desired enzymes by the microorganism.

12. The method according to claim 9 wherein the microorganism is cultivated at a pH of from about 4.0 to about 9.5 and a temperature of from about 20° C. to about 40° C. and the reaction mixture is incubated at a pH of from about 6.0 to about 9.5 and a temperature of from about 20° C. to about 40° C.

13. The method according to claim 1 wherein D(−)-β-hydroxyisobutyric acid is recovered from the aqueous medium by solvent extraction.

14. The method according to claim 13 wherein the solvent extraction is carried out by adjusting the pH of the aqueous medium to within the range of from about 1 to about 4, adding inorganic salt and then extracting D(−)-β-hydroxyisobutyric acid with a water-immiscible solvent.

15. The method according to claim 13 wherein the solvent extraction is carried out by adjusting the pH of the aqueous medium to within the range of from about 8 to about 10, extracting the unutilized substrate from the aqueous medium with a water-immiscible solvent, adjusting the pH of the resulting aqueous phase to within the range of from about 1 to about 4, adding inorganic salt and extracting D(−)-β-hydroxyisobutyric acid with a water-immiscible solvent.

16. A method for producing D(−)-β-hydroxyisobutyric acid, which comprises subjecting a substrate which is isobutyl-isobutyrate, alone or mixtures thereof with isobutyl methacrylate, to the action of a microorganism having the ability to convert the substrate into D(−)-β-hydroxyisobutyric acid in an aqueous medium and recovering D(−)-β-hydroxyisobutyric acid from the medium, said microorganism being cultivated in aqueous medium in the presence of isobutyl-isobutyrate, said microorganism belonging to a genus selected from the group consisting of the genus Candida, Saccharomyces, and Aspergillus.

17. The method according to claim 16 wherein the substrate is isobutyl-isobutyrate.

18. The method according to claim 16 wherein said microorganism belongs to the species Candida rugosa.

19. The method according to claim 16 wherein D(−)-β-hydroxyisobutyric acid is recovered from the aqueous medium by solvent extraction.

20. The method according to claim 19 wherein the solvent extraction is carried out by adjusting the pH of the aqueous medium to within the range of from about 1 to about 4, adding inorganic salt and then extracting D(−)-β-hydroxyisobutyric acid with a water-immiscible solvent.

21. The method according to claim 19 wherein the solvent extraction is carried out by adjusting the pH of the aqueous medium to within the range of from about 8 to about 10, extracting the unutilized substrate from the aqueous medium with a water-immiscible solvent, adjusting the pH of the resulting aqueous phase to within the range of from about 1 to about 4, adding inorganic salt and extracting D(−)-β-hydroxyisobutyric acid with a water-immiscible solvent.

* * * * *